(12) United States Patent
van Rijn et al.

(10) Patent No.: US 9,545,471 B2
(45) Date of Patent: Jan. 17, 2017

(54) EXTRACORPOREAL FLUIDIC DEVICE FOR COLLECTING CIRCULATING TUMOR CELLS AND METHOD OF USE THEREOF

(71) Applicant: VIATAR LLC, Lowell, MA (US)

(72) Inventors: Cornelis Johannes Maria van Rijn, Hengelo (NL); Ilan K. Reich, Short Hills, NJ (US)

(73) Assignee: VIATAR LLC, Lowell, MA (US)

( * ) Notice: Subject to any disclaimer, the term of this patent is extended or adjusted under 35 U.S.C. 154(b) by 295 days.

(21) Appl. No.: 14/452,828

(22) Filed: Aug. 6, 2014

(65) Prior Publication Data
US 2015/0041398 A1    Feb. 12, 2015

Related U.S. Application Data

(60) Provisional application No. 61/862,864, filed on Aug. 6, 2013.

(51) Int. Cl.
*A61M 1/34* (2006.01)
*B01D 61/00* (2006.01)

(52) U.S. Cl.
CPC ......... *A61M 1/3482* (2014.02); *A61M 1/3431* (2014.02); *A61M 1/3472* (2013.01); *A61M 1/3486* (2014.02); *A61M 1/342* (2013.01); *A61M 2202/005* (2013.01); *A61M 2202/0014* (2013.01); *A61M 2202/0057* (2013.01); *A61M 2205/75* (2013.01)

(58) Field of Classification Search
None
See application file for complete search history.

(56) References Cited

U.S. PATENT DOCUMENTS

| | | | |
|---|---|---|---|
| 3,977,995 A | 8/1976 | Louderback et al. | |
| 4,296,373 A | 10/1981 | Angel et al. | |
| 5,067,491 A | 11/1991 | Taylor et al. | |
| 5,556,764 A | 9/1996 | Sizto et al. | |
| 5,753,014 A | 5/1998 | Van Rijn | |
| 5,962,238 A | 10/1999 | Sizto et al. | |
| 6,231,536 B1 * | 5/2001 | Lentz | A61K 31/00 |
| | | | 128/898 |

(Continued)

FOREIGN PATENT DOCUMENTS

| | | |
|---|---|---|
| WO | WO 2004/000444 | 12/2003 |
| WO | WO 2005/105276 | 11/2005 |
| WO | WO 2006/116327 | 11/2006 |
| WO | WO 2006/127256 | 11/2006 |

(Continued)

OTHER PUBLICATIONS

Zheng et al, Membrane microfilter device for selective capture, electrolysis and genomic analysis of human circulating tumor cells:, Journal of Chromatography A, May 29, 2007.*

(Continued)

*Primary Examiner* — Krishnan S Menon
(74) *Attorney, Agent, or Firm* — Potomac Law Group, PLLC; Mark Catan

(57) ABSTRACT

A device can be used to retain circulating tumor cells (CTCs). The device can include a cross-flow module with a retentate channel and a permeate channel. A filter in the cross-flow module can separate the retentate channel from the permeate channel. The filter can be constructed such that CTCs are retained in the retentate channel while other cells can pass through the filter into the permeate channel. A recirculation channel can direct a flow from an outlet of the retentate channel back to an inlet of the retentate channel to thereby concentrate CTCs in the retentate flow.

19 Claims, 4 Drawing Sheets

(56) References Cited

U.S. PATENT DOCUMENTS

| | | | |
|---|---|---|---|
| 6,350,619 | B1 | 2/2002 | Mercolino et al. |
| 6,622,872 | B1 | 9/2003 | Tai et al. |
| 6,974,692 | B2 | 12/2005 | Chang |
| 7,136,152 | B2 | 11/2006 | Bruls et al. |
| 7,695,966 | B2 | 4/2010 | Raz |
| 7,738,094 | B2 | 6/2010 | Goldberg |
| 7,846,393 | B2 | 12/2010 | Tai et al. |
| 2006/0254972 | A1 | 11/2006 | Tai et al. |
| 2008/0248182 | A1 | 10/2008 | Jongsma et al. |
| 2008/0318324 | A1* | 12/2008 | Chiu ................ B01D 63/00 436/64 |
| 2011/0053152 | A1* | 3/2011 | Goldkorn ............ C12N 5/0693 435/6.14 |
| 2014/0074007 | A1* | 3/2014 | McNeil ............... A61M 1/3486 604/4.01 |

FOREIGN PATENT DOCUMENTS

| | | |
|---|---|---|
| WO | WO 2008/008515 | 1/2008 |
| WO | WO 2011/150357 | 12/2011 |
| WO | WO 2012/065185 | 5/2012 |

OTHER PUBLICATIONS

Girones et al., "Flux stabilization of silicon nitride microsieves by backpulsing and surface modification with PEG moieties," *Journal of Colloid and Interface Science*, 2006, 299(2):pp. 831-40.

Hasebe et al., "Effects of surface roughness on anti-thrombogenicity of diamond-like carbon films," *Diamond and Related Materials*, 2007, 16.4:pp. 1343-1348.

International Search Report and Written Opinion, dated Jul. 18, 2011, for International Application No. PCT/US11/30741.

Nan et al., "Blood compatibility of amorphous titanium oxide films synthesized by ion beam enhanced deposition," *Biomaterials*, 1998, 19.7-9:pp. 771-776.

Stott et al., "Isolation of circulating tumor cells using a microvortex-generating herringbone-chip," *Proceedings of the National Academy of Sciences*, 2010, 107(43): pp. 18392-18397.

Van Rijn et al., "A Microsieve for Leukocyte Depletion of Erythrocyte Concentrations," *18th Annual International Conference of the IEEE*, Amsterdam, 1996, 1:pp. 256-257.

Vona et al., "Isolation by Size of Epithelial Tumor Cells: A New Method for the Immunomorphological and Molecular Characterization of Circulating Tumor Cells," *American Journal of Pathology*, 2000, 156(1):pp. 57-63.

Yuan et al., "Improvements of blood compatibility on cellulose membrane surface by grafting betaines," *Colloids and Surfaces B: Biointerfaces*, 2003, 30(1-2): pp. 147-155.

Zhang et al., "Superlow fouling sulfobetaine and carboxybetaine polymers on glass slides," *Langmuir*, 2006, 22.24:pp. 10072-10077.

Zheng et al., "3D microfilter device for viable circulating tumor cell (CTC) enrichment from blood," *Biomed Microdevices*, 2011, 13:pp. 203-213.

Zheng et al.,"Membrane microfilter device for selective capture, electrolysis and genomic analysis of human circulating tumor cells," *Journal of Chromatography A*, 2007, 1162(2): pp. 154-161.

\* cited by examiner

EXTRACORPOREAL FLUIDIC DEVICE FOR COLLECTING CIRCULATING TUMOR CELLS AND METHOD OF USE THEREOF

FIELD

The present disclosure relates generally to blood processing, and, more particularly, to extracorporeal blood processing for collecting circulating tumor cells.

SUMMARY

Systems, methods, and devices for collecting circulating tumor cells using an extracorporeal fluidic device are disclosed herein.

In embodiments, a device for retaining circulating tumor cells (CTCs) can include a retentate channel, a permeate channel, a first filter, and a recirculation channel. The first filter can separate the retentate channel from the permeate channel. The first filter can be constructed such that CTCs are retained in the retentate channel while other cells pass through the first filter to the permeate channel. The recirculation channel can direct a flow from an outlet of the retentate channel to an inlet of the retentate channel.

In embodiments, a method of treating a patient can include connecting a patient's blood stream to a circulating tumor cell (CTC) device. The CTC device can include a cross-flow module and a recirculation channel. The cross-flow module can include a retentate channel, a permeate channel, and a CTC retention filter. The retentate channel can have respective inlet and outlet ends. The permeate channel can be adjacent to the retentate channel and can have respective inlet and outlet ends. The CTC retention filter can separate the permeate and retentate channels and can be constructed to retain at least CTCs. The recirculation channel can connect the retentate channel outlet end with the retentate channel inlet end. The recirculation channel can also include a treatment element. The method can further include filtering blood using the CTC retention filter so as to retain at least white blood cells and CTCs and concentrating the CTCs in the fluid in the retentate channel. The blood in the permeate channel can be returned to the patient.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements.

DETAILED DESCRIPTION

In embodiments of the disclosed subject matter, a statistically significant quantity of circulating tumor cells (CTCs), for example, on the order of $10^2$ to $10^5$ cells, can be captured from a patient's blood or other bodily fluid. Captured CTCs can then be used for a broad range of research and clinical uses, such as drug trial validation, therapeutic decisions, genetic research to determine the DNA of a given cancer variant (both for the primary and secondary tumors) and the pace and character of its mutations, and diagnostic, drug discovery and/or therapeutic methods.

In embodiments of the disclosed subject matter, 100 mL to 5 L of peripheral or central venous blood can be circulated in an extracorporeal circuit. Live CTCs can be separated from the circulating blood using a filter. The normal blood components can then be returned to the patient. The removal of CTCs may provide important diagnostic and therapeutic effects. In addition, the capture and removal of CTCs may allow for improved drug discovery by providing a pool of viable human CTCs for subsequent research.

Figure 1:
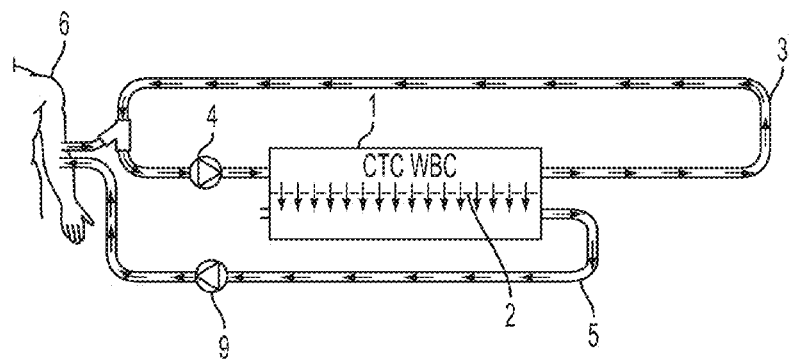
FIG. 1 shows an extracorporeal circulating tumor cell (CTC) cross-flow filtration device with permeate and retentate fluid lines in which a retentate fluid is recirculated, according to certain embodiments of the disclosed subject matter.

FIG. 1 shows an extracorporeal CTC cross-flow filtration device, according to one or more embodiments, including permeate and retentate fluid lines in which a retentate flow is recirculated. Permeate fluid lines refer to the lines carrying fluid that has passed through a cross-flow filter, while retentate fluid lines refer to the lines recirculating the fluid that has not passed through the filter. The retentate fluid lines can be used to form a circuit that brings the unfiltered bodily fluid from the patient 6 to a cross-flow module 1. The cross-flow module 1 can separate the CTCs and white blood cells (WBCs) from the fluid, and the bodily fluid containing the CTCs and WBCs can then be recirculated from the exit of the cross-flow module 1 back to the entrance of the module, where it can be combined with additional unfiltered bodily fluid from the patient 6. The permeate fluid lines can form a circuit that takes the filtered bodily fluid that passes through the cross-flow filter 2 in the cross-flow module 1 and returns the fluid to the patient 6.

In various embodiments, the extracorporeal filtration device can comprise a cross-flow filter module 1 having inlet and outlet ends and a CTC cross-flow filter 2. The device can further comprise retentate fluid lines 3 for recirculating fluid that does not pass through the CTC cross-flow filter 2. The retentate fluid lines 3 can connect the retentate outlet of the filter module 1 with the retentate inlet of the filter module 1. The device can further comprise a recirculation pump 4, and a permeate fluid line 5 for returning fluid that has passed through the CTC cross-flow filter 2 back to the patient 6, e.g., via a vascular access and pump 9.

The CTC cross-flow filter 2 can have, for example, round pores with a diameter between about 3 µm and 8 µm (e.g., about 3 µm, 4 µm, 5 µm, 6 µm, 7 µm, or 8 µm, or any size in between), or slit-shaped pores with a width between 3 µm and 8 µm (e.g., about 3 µm, 4 µm, 5 µm, 6 µm, 7 µm, or 8 µm, or any size in between) and a length between 3 µm and 40 µm. The specific shape and dimensions of the pores can be chosen for substantially complete permeation of red blood cells (RBCs) and platelets while retaining a significant fraction of CTCs and WBCs. Repetitive recirculation of the retentate over the cross-flow filter 2 can concentrate the retentate with increasing quantities of CTCs and WBCs. Concentration methods encompass any method that results in a fluid or fluid sample having an increased concentration of CTCs after application of the method, as compared to the initial concentration prior to the method.

In certain embodiments, the cross-flow filter 2 is a microsieve. For example, the microsieve is a flat, rigid filter device manufactured by semiconductor fabrication technologies. In certain embodiments, the semiconductor fabrication can produce a filter having a large number of precise filter pores of arbitrary geometry and pattern by etching through very thin layers of, e.g., silicon nitride, applied to a monocrystalline silicon wafer. Such filters are described, for example, in U.S. Publication No. 2011/0244443, published Oct. 6, 2011 and entitled "Methods, Systems and Devices for Separating Tumor Cells," which is hereby incorporated by reference herein in its entirety. Other filter materials can also be used, such as polymeric materials, silicon, silicon nitride, silicon oxide, diamond-like carbon, or any other suitable material having sufficient structural strength to support a thin surface having a high percentage porosity and capable of remaining intact when exposed to a bodily fluid under pressure.

In certain embodiments, the filter 2 has a smooth flat polished surface with regularly spaced straight pores with an aspect ratio (ratio of the axial length to diameter) of no more than ten, or of no more than two. With such a filter having a round pore size of e.g., about 3 µm, 4 µm, 5 µm, 6 µm, or 7 µm, high concentrations of CTCs and WBCs can be achieved. For example, the retained bodily fluid that does not pass through the filter (i.e., the retentate fluid or retentate) can comprise concentrations of about 25-100% of the CTCs and 10-70% of the WBCs in the original bodily fluid. The concentrated species in the recirculation channel can be drained and collected for analysis or for further fractionation.

Figure 2:
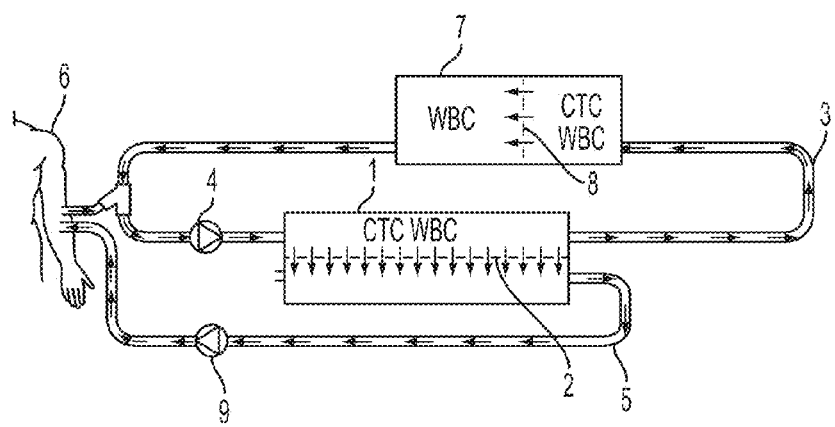
FIG. 2 shows another extracorporeal CTC filtration device in which a retentate processor element is incorporated in a retentate fluid line, according to certain embodiments of the disclosed subject matter.

In some embodiments, the retentate with WBCs and CTCs can be separated in a second stage using a further filter element or a cascade of filter elements with pore sizes between 3 µm and 30 µm (e.g., a first filter having pores with a diameter of 30 µm, a second filter having pores with a diameter of 20 µm, a third filter having pores with a diameter of 10 µm, etc.). Different fractions will then contain different ratios of CTCs and WBCs. Fractions free of CTCs, but with high amounts of the patient's own immune system cells can be transferred back to the permeate flow channel or directly to the patient 6. As depicted in FIG. 2, a retentate processor or treatment chamber 7 (e.g., including a further filter element 8) for separating CTCs from WBCs can be directly incorporated in the recirculation channel 3, which is able to separate the CTCs from the WBCs. The separated WBCs can then be returned to the patient 6. In some embodiments, the WBCs have been exposed to a high concentration of CTCs in the retentate fluid prior to filtering and return to the patient 6. Thus, the WBCs may be used for immunotherapy because they have an increased ability to recognize and scavenge CTCs after being returned to the patient 6.

Figure 3:
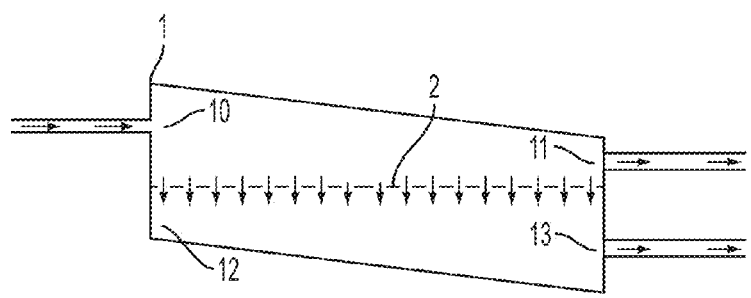
FIG. 3 shows a module design of a CTC cross-flow filter, according to certain embodiments of the disclosed subject matter.

FIG. 3 shows an exemplary design of a CTC cross-flow filter module 1. The module can comprise an entrance 10 for an unfiltered fluid. The bodily fluid passes across the module, with the retentate fluid passing above the filter 2 and then exiting at 11 through the retentate fluid line, while the permeate fluid passes through the filter 2, increasing in volume as the fluid travels from an inlet end 12 through the module, and exiting at 13 via the permeate fluid line. In some embodiments, the module can comprise a channel for the permeate fluid (i.e., permeate channel) that has a height at the beginning of the channel between, e.g., 100 µm and 500 µm, and which increases along the channel. In some embodiments, the module can comprise a channel for the retentate fluid (i.e., a retentate channel) that has a height at the beginning of the channel between, e.g., 100 µm and 500 µm, and which decreases along the channel.

Figure 4:
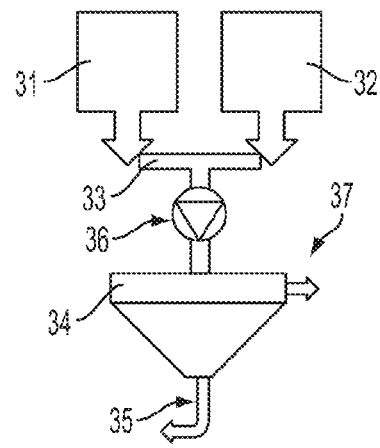
FIG. 4 shows an extracorporeal CTC filtration device with a container of bodily fluid containing CTCs extracted from a patient, according to certain embodiments of the disclosed subject matter.

FIG. 4 shows an exemplary dead end filtration device which combines whole blood 31 (e.g., blood donated by a patient) with a physiologically-appropriate dilution fluid 32 (e.g., saline) in a metering compartment 33 to set an appropriate hematocrit level at the filter module 34. An infusion pump or other mechanical device 36 may be used to volumetrically control the amount of fluid passing through the filter module 34. Alternatively, in some embodiments, this system works by gravity flow (using a fixed height for the containers holding the blood 31 and the dilution fluid 32). The hematocrit level can be established using the metering component 33 and an active control system, for example, to vary the flow from the blood 31 and/or dilution fluid 32 containers based on feedback from pressure sensors above and/or below the filter module 34 with the goal of maintaining a predetermined transmembrane pressure.

The design shown in FIG. 4 is suitable for collecting a significant quantity of CTCs from up to 500 mL of blood, and returning it safely to the patient, e.g., via return line 35, since the amount of dilution fluid 32 added to the blood or other bodily fluid being returned to the patient is not excessive. A dilution fluid to reduce the hematocrit of the blood being processed can be an efficient means for avoiding the need for a larger filter, thereby reducing the cost and improving the efficacy of this technique of CTC collection. In various embodiments, the concept of pre-dilution shown in FIG. 4 is also applicable to all of the cross-flow designs shown, for example, in FIGS. 1-3.

The cross-flow outlet can have an enriched CTC concentrate 37 fraction that can be used for diagnostics or therapeutic purposes. It has been found advantageous to predilute the blood from the patient before applying cross-flow filtration. Both the fraction of CTCs and WBCs have been found higher when using a predilution fluid in specific cross-flow settings. It may be assumed that the blood cells and CTCs behave more as semi-rigid and/or isolated microspheres in diluted blood, which favors the cross-flow filtration process.

Figure 5:
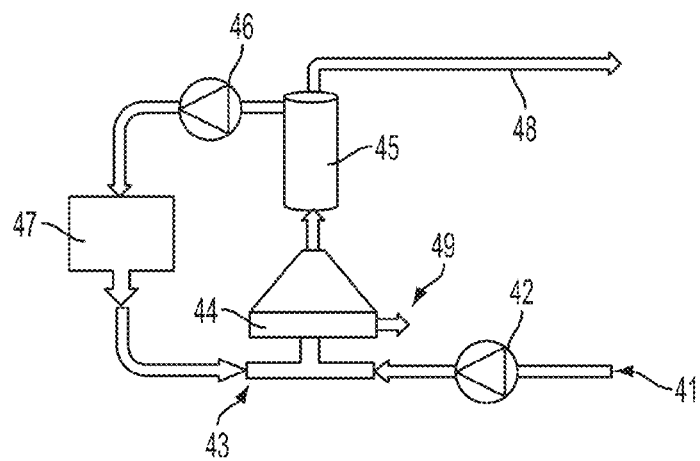
FIG. 5 shows an extracorporeal CTC filtration device which pre-dilutes bodily fluid from a patient, according to certain embodiments of the disclosed subject matter.

FIG. 5 shows an exemplary dead end filtration device which overcomes potential limitations on the volume of bodily fluid that can be processed (e.g., 500 mL of blood). Such a limitation on bodily fluid volume may be present in certain embodiments, such as that shown in FIG. 4. In the context of a therapeutic CTC application, where the goal is to process a patient's entire blood volume (e.g., 5 L) or other bodily fluid in a single session and return it safely to the patient, it may be impractical and unsafe to return the dilution fluid to the patient. The embodiment of FIG. 5 provides for a recirculation loop for the dilution fluid, such that the blood or other bodily fluid is pre-diluted just before the CTC filter module 44, but the added dilution fluid 43 is then removed via convection using a conventional membrane filter 45 (e.g., an ultrafilter) and returned to the reservoir of dilution fluid 47 for reuse, for example, via an effluent pump 46. Therefore, the blood or other bodily fluid returned to the patient, e.g., along return line 48, is equivalent in volume, electrolyte balance and/or other characteristics as the incoming blood from the patient, e.g., via blood pump 42 and supply line 41, minus the CTCs and WBCs removed via the CTC filter module 44. The cross-flow outlet can have an enriched CTC concentrate 49 fraction that can be used for diagnostics or therapeutic purposes. It has also been found in this case that it is advantageous to predilute the blood from the patient before applying cross-flow filtration. Both the fraction of CTCs and WBCs have been found higher when using a predilution fluid in specific cross-flow settings.

In various embodiments, the conventional membrane filter 45 can have a very low molecular weight cut-off (e.g., less than 50 Daltons, less than 100 Daltons, less than 500 Daltons, or less than 1,000 Daltons), or chemical affinity modifications (including antibodies) to retain cytokines or other materials, in order to achieve a specific composition of the blood or other bodily fluids returned to the patient. In various embodiments, the concept of recirculation of the dilution fluid shown in FIG. 5 is also applicable to all of the cross-flow designs shown, for example, in FIGS. 1-3.

In some embodiments, the filtering devices and methods disclosed herein can be used to filter about 70-100%, or about 90-99% (e.g., at least about 70, 75, 80, 85, 90, 95, 99, 99.5, or 99.9%, or any value in between) of the blood or other bodily fluid from the patient 6 via peripheral or central venous vascular access after the first passage through the cross-flow filter 2. The filtered fluid enters the permeate channel and is returned to the patient. The remaining blood or other bodily fluid is retained in the recirculation channel. For example, this can mean, in terms of blood flow rates, that if via the vascular access 100 ml/min is drawn from the patient 6, then the flow rate of the recirculating retentate can be set at 1-10 ml/min in steady state with aid of a recirculation pump 4 in order to allow for sufficient fluid to pass through the filter 2 to filter at least about 70% of the fluid on the first pass.

The flow rate of the permeate fluid, as it is returned to the patient 6 in steady state, can be set with aid of the permeate pump 9 to the same rate as the vascular access flow rate drawn from the patient (e.g., 100 ml/min). To set the flow rate of the recirculating retentate fluid at a relatively low value may provide a number of advantages, including that the CTCs and WBCs will have a longer interaction time to recognize each other, and it will be easier to separate the CTCs from the WBCs in the second filtering step using, e.g., the filter 8 in treatment chamber 7. In addition, the number of passages through the recirculation pump can be minimized, or at least reduced.

Many process variations are possible. In some cases the blood that is free of CTCs coming out the treatment chamber 7 can be directly returned to the patient, or in some cases, the retentate fraction is so low with respect to the permeate fraction that it is not necessary to recirculate the retentate fraction with the aid of a recirculation pump 4.

In certain embodiments, the retentate channel has a tapered cross-section in order to maintain a constant shear rate as the retentate fluid flows through the filter module 1. Because a large fraction of the bodily fluid will permeate through the cross-flow filter 2, it may be desirable to lower the channel height of the retentate channel near the retentate exit 11 with respect to the retentate inlet 10, as shown in FIG. 3. For example the cross-flow channel height might taper from 100 µm to 50 µm along the cross-flow channel. Normal fluid mechanics can be used to calculate the shear rate along the retentate flow channel and to implement an adequate tapering of the retentate channel from inlet 10 to outlet 11 or design other dimensional aspects (e.g., width, length and fixed channel height).

Likewise the permeate channel may have a tapered cross-section from one end 12 to the outlet end 13 in order to compensate and/or to maintain a constant trans-membrane pressure over the cross flow filter 2.

In certain embodiments, the cross-flow filter, pumps and channels are sized such that a stable permeate flow of blood (e.g., the fluid depleted of CTCs) that is at least 80% of the flow of blood entering the filter module may be achieved.

In some embodiments, the permeate and/or the retentate flow channel is a rectangular, rhomboidal, or tetrahedral flow channel, or is formed in other similar shapes to provide for a constant shear rate and trans-membrane pressure. In some embodiments, the filter module has a length equivalent to the length of the cross-flow filter contained within the module. In some embodiments, the filter has a length that is at least ten times the channel height or width.

In some embodiments, the retentate fluid flow has a predefined mean shear rate of at least about 100 $s^{-1}$ (e.g., at least about 100 $s^{-1}$, 200 $s^{-1}$, 500 $s^{-1}$, 1000 $s^{-1}$, 2000 $s^{-1}$, or 5000 $s^{-1}$, or any value in between).

In some embodiments, the permeate and retentate channels are able to maintain a constant ratio of the transmembrane pressure and the shear rate along the CTC filter.

In some embodiments, the permeate channel has a height between about 200 µm and 500 µm, and the retentate channel has a height between about 50 µm and 500 µm.

In various embodiments, the systems and methods described above can be used in a method of treating blood or other bodily fluid, comprising: determining a shear rate range and a trans-membrane range along a flow path of the blood along a filter. The objective is to maximize the useful area of the filter, avoid different transmembrane pressures at different points along the filter, and/or maintain a low transmembrane pressure so as to avoid damage to cells and fouling of the filter. In these instances, the filter would be configured to retain at least WBCs and CTCs; passing blood or other bodily fluid through the filter in a cross-flow direction to retain at least WBCs and CTCs therefrom; collecting the retentate fluid, in particular the CTCs resulting from said filtering; and returning the permeate fluid to a patient. In some embodiments, the filtering method can be repeated continuously for processing at least 1 L of blood. In certain embodiments, the flux of permeate fluid passing through the cross-flow filter 2 is between about 0.2 ml/cm²/min and 20 ml/cm²/min (e.g., about 0.2 ml/cm²/min, 0.5 ml/cm²/min, 1.0 ml/cm²/min, 2.0 ml/cm²/min, 5.0, ml/cm²/min 10.0 ml/cm²/min, or 20 ml/cm²/min, or any value in between).

Figure 6:
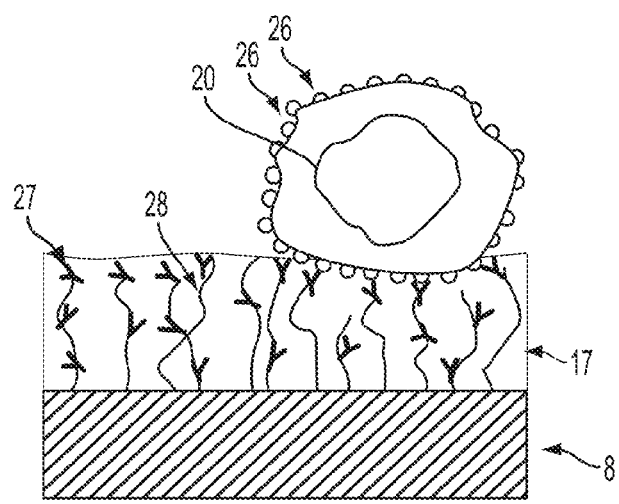
FIG. 6 shows an antibody coating applied on a retentate processor element or on a CTC filter, according to certain embodiments of the disclosed subject matter.

In some embodiments, the recirculation channel 3 can comprise a retentate processor or treatment chamber 7 that is able to separate CTCs from WBCs. This chamber 7 can preferentially bind or retain CTCs with respect to other blood or other cells present in the recirculation channel 3. In some embodiments, the treatment chamber 7 retains CTCs using a filter 8 that uses size-based filtration to retain CTCs, while allowing passage of other cells in the bodily fluid. In some embodiments, the treatment chamber 7 retains CTCs using one or more (e.g., one, two, three, four, five or more) different types of antibodies that are specific for CTCs. For example, many types of CTCs 20 are of epithelial origin and express EPCAM 26. Accordingly, in some embodiments, the treatment chamber 7 can bind CTCs 20 via an anti-EPCAM antibody, anti-EFGR antibody, or other antibody-CTC interaction mechanism, as depicted in FIG. 6.

In some embodiments, the antibodies 27 are bound to a blood compatible hydrogel layer 17 composed of polymer chains 28, with a length typically between 500 nm and 5 μm, capable in binding a large number of antibodies 27 per polymer chain 28. The coating 17 can provide a three-dimensional surface structure in which the chains 28 of the hydrophilic polymer are aligned at least partly vertical to the substrate surface, e.g., brush-like. Due to their increased surface compared to planar structures, such brush-like hydrogel surfaces show a particularly enhanced immobilization capacity for biomolecules, such as antibodies and other affinity molecules which are capable of binding the target cells. It has been found that brush-like structured hydrogel coatings, in particular those which comprise or consist of certain polycarboxylate polymers, provide an excellent surface for selectively attaching cells to a solid support for subsequent detection and/or quantification.

The hydrogel coating 17 can be of any thickness which allows for the capture of the target cells 20 on the surface of the hydrogel. For example, the hydrogel coating 17 has a thickness of between about 100 nm and about 5000 nm, for example between about 500 nm and about 3000 nm. The thickness of the coating can be determined by routine methods known in the art, for example, by atomic force microscopy (AFM) or ellipsometry. Very good results have been obtained with a slightly cross-linked and very open polycarboxylate network layer provided on the filter 8 (e.g., a microsieve). Part of the blood flow will pass through the open network, herewith increasing the probability of close contact between the antibodies immobilized in the open network and the antigen presenting CTCs in the sample fluid. The open porosity (i.e., the fraction of the volume of voids over the total volume) of the open network can be between 30% and 99.9%, for example, between 80% and 99%.

To reduce the number of non-specific binding events to the antibody functionalized polymeric network layer, two additional measures have been found advantageously. The first measure is to form polycarboxylate polymers with side groups of polyethyleneglycol. The second measure is to form polycarboxylate polymers with side groups of zwitterions, such as phosphocholine and carboxybetaine groups.

In some embodiments, the treatment chamber 7 includes a surface with antibodies or an antibody-coated surface. This can be accomplished via immobilization of functional antibodies 27 on a flow along (e.g., FIG. 7) substrate (e.g., in coating 17) where fluid flows parallel to a surface containing the immobilized antibodies, or a flow-through substrate (e.g., FIG. 8) where fluid flows through a filter 8 or other membrane (e.g., a microsieve with a pore size larger than 10 μm, for example, larger than 20 μm) coated with the immobilized antibodies (e.g., in coating 17). In either the flow-along or flow-through options, the treatment chamber 7 allows passage of all other blood cells, such as monocytes and macrophages 21, natural killer cells (NK cells) and lymphocytes 22, erythrocytes and thrombocytes 23, except for CTCs 20.

Figure 7:
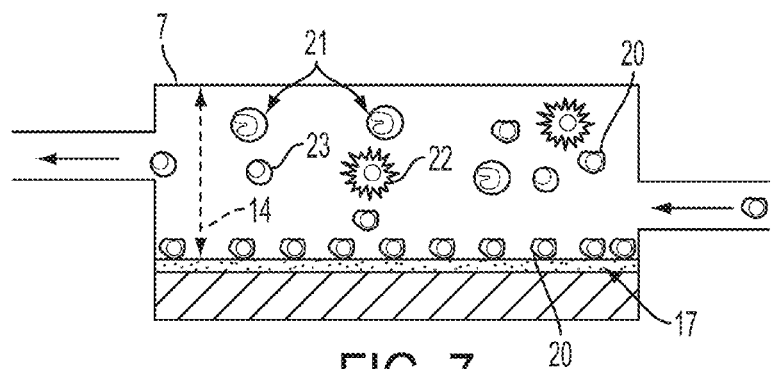
FIG. 7 shows a CTC-affinity filter design for a retentate processor element, according to certain embodiments of the disclosed subject matter.

In FIG. 7, an exemplary flow-past configuration is depicted. In some embodiments, after capture of the CTCs 20 on surface 17 (e.g., coating) by the immobilized antibodies 27, there will be interaction with CTCs, as the blood cells 20-23 pass by. In particular T-lymphocytes and natural killer cells 22 being in close contact with CTCs 20 can become activated and may stimulate the patient's own immune system to attack the CTCs 20. In some cases, it may be desirable to temporarily uncouple the treatment chamber 7 from the recirculation channel 3 for further treatment, for example to optimize the activation of a patient's own immune system. The treatment chamber 7 can also be provided with added cytokines, such as IL8, IL12, IL15 and interferon, to stimulate and mature the NK cells 22 to attack the CTCs 20. Through such methods, a large synergy can be obtained because both CTCs 20 and patients own immune cells 21, 22 are concentrated in the retentate fluid. In some embodiments, cytokines can be added to the retentate fluid in the treatment chamber 7. For the flow-along device as shown in FIG. 7, a low channel height 14 (e.g., less than 500 μm) can provide a better likelihood of binding of CTCs.

Figure 8:
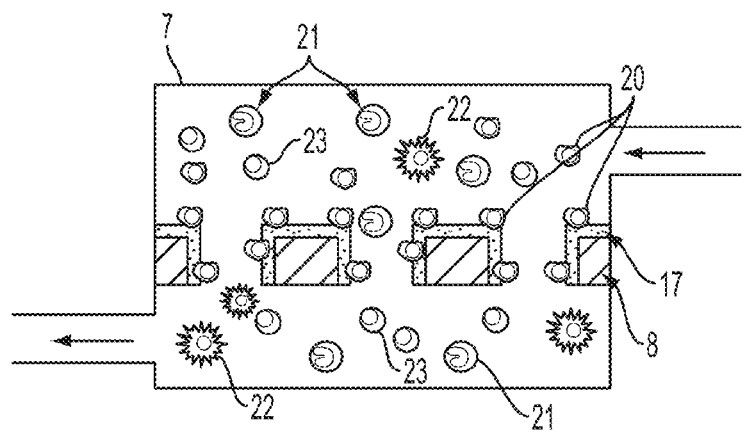
FIG. 8 shows further variations of a CTC-affinity filter, according to certain embodiments of the disclosed subject matter.

In some embodiments, a flow-through device as illustrated in FIG. 8 can have advantages over the flow-along device as illustrated in FIG. 7. For example, in the flow-through device, all the CTCs 20 will have a better interaction with the antibody layer 17 provided on the microsieve 8. The interaction time of the CTCs with the antibodies is dependent on the flow rate through the filter 8. In some embodiments, the capture efficiency of the treatment chamber 7 is dependent mainly on the flow rate of the blood cell suspension and the open porosity (i.e., fraction of open pore area with respect to total area) of the filter 8. This means that the pore sizes on the antibody-coated filter 8 can be chosen, in some embodiments, to be larger than the size of the largest WBCs (monocytes and macrophages), which allows easy permeation of most or all the WBCs through the microsieve 8. In some embodiments, the flow-through treatment element is an antibody-coated 17 microsieve 8 with a pore size larger than 10 μm, or larger than 20 μm. In some embodiments, the antibodies 27 are bound to a blood compatible hydrogel layer 17 composed of polymer chains 28, with a length typically between 500 nm and 5 μm, capable of binding a large number of antibodies 27 per polymer chain 28.

EXAMPLES

Example 1

Dimensions of Captured CTCs

Figure 9:
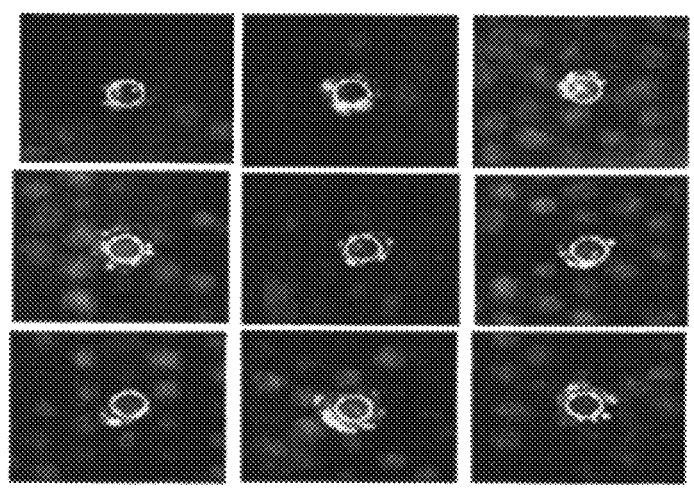
FIG. 9 is a series of pictures illustrating capture of small cell lung cancer cells using a microsieve filter.

The effectiveness of size-based filtration was evaluated using silicon nitride microsieves, each containing either 3.5 μm or 5 μm round pores. The level of CTC capture and the dimensions of captured CTCs were evaluated using high-power microscopy. Cell lines and patient samples containing small cell lung cancer, prostate cancer, and bladder cancer were applied to the microsieve. The captured CTCs were generally at least 8 μm in diameter for all cancer cell types. For example, FIG. 9 shows the capture of nine small cell lung cancer cells on a 5 μm microsieve filter. The captured CTCs were 7-9 μm in diameter.

Table 1 shows the dimensions of captured bladder cancer cells from twelve samples of J82 cells using microsieves having 3.5 μm round pores. None of the captured cells was smaller than 12 μm, and several were larger than 16 μm.

TABLE 1

Dimensions of captured bladder cancer cells

| Sample ID | Cell Length (μm) | Cell Width (μm) |
|---|---|---|
| J82-1 | 16.9 | 15.2 |
| J82-2 | 15.5 | 16 |
| J82-3 | 26 | 24 |
| J82-4 | 19.5 | 16.7 |
| J82-5 | 15.7 | 15.5 |
| J82-6 | 17 | 13 |
| J82-7 | 17.1 | 15.2 |
| J82-8 | 18.1 | 17.4 |
| J82-9 | 13.6 | 12.4 |
| J82-10 | 20.5 | 19.5 |
| J82-11 | 19.1 | 19 |

Table 2 shows the estimated dimensions of captured prostate cancer cells from eight human samples using the CELLSEARCH™ platform. The captured cells ranged in diameter from 4 to 12 μm, with a median diameter of 8 μm.

TABLE 2

Dimensions of captured prostate cancer cells

| PID | CTC Size Estimate | | |
|---|---|---|---|
| | Low (μm) | High (μm) | Median (μm) |
| 114-1 | 5 × 6 | 12 × 16 | 8 × 10 |
| 114-2 | 5 × 6 | 12 × 16 | 8 × 10 |
| 127-1 | 5 × 8 | 8 × 15 | 8 × 10 |
| 114-4 | 6 × 6 | 10 × 18 | 8 × 10 |
| 133-1 | 5 × 6 | 8 × 11 | 8 × 9 |
| 114-5 | 5 × 6 | 10 × 18 | 8 × 10 |
| Satra006EOT | 4 × 5 | 10 × 10 | 6 × 8 |
| 110-3 | 5 × 5 | 8 × 12 | 8 × 8 |

Example 2

Filtration Efficiency

To evaluate the efficiency of size-based filtration, microsieves having pores of various sizes were tested using both cultured prostate cancer cells and CTCs from human cancer patients. Cells were added (i.e., "spiked") into blood from human donors. As a control, human blood with no CTCs was also passed through the microsieves. None of the microsieves captured cells in the control runs. Table 3 shows the capture efficiency of microsieves having pores of size 3 μm×8 μm, 3.5 μm×8 μm, 3.5 μm×12 μm, 4 μm×8 μm, and 4 μm×12 μm (microsieves A, C, D, E, and F, respectively). All the microsieves were uncoated. Each microsieve was evaluated up to four times, and the maximum pressure and the percentage of spiked calls that were captured is indicated in Table 3.

TABLE 3

Results of microsieve capture efficiency tests

| Filter Type Microsieve | Run A | | Run B | | Run C | | Run D | | Run E | |
|---|---|---|---|---|---|---|---|---|---|---|
| | Max Torr | Cell Count | Max Torr | Cell Count | Max Torr | Cell Count | Max Torr | Cell Count | Max Torr | Cell Count |
| A (3 × 8 μm) | | | 65.88 | | 67.4 | | 65.9 | | 65.1 | |
| C (3.5 × 8 μm) | 46.6 | 40/50 (80%) | 39.63 | 24/45 (53%) | 59.6 | 35/50 (70%) | 61 | 36/50 (72%) | 59.5 | 26/50 (52%) |
| D (3.5 × 12 μm) | 59.2 | 25/50 (50%) | 30.2 | 15/45 (33%) | 62.2 | 28/50 (54%) | 38.2 | 31/50 (62%) | 44.6 | 13/50 (26%) |
| E (4 × 8 μm) | 38.4 | | 19.77 | | | | | | | |
| F (4 × 12 μm) | 29.6 | 26/50 (52%) | 11.77 | 17/45 (37%) | 28.9 | 14/50 (28%) | 15.2 | 5/50 (10%) | 26.2 | 12/50 (24%) |

Capture efficiency ranged from 10 to 80% of the spiked cells in the sample, independent of cancer type. Based on the data shown above, a larger pore size is preferable due to the significant capture rate (50%) and higher blood flow rate. Further, size-based filtration can capture a significant percentage of CTCs provided that the pressure is kept fixed at a low value between 5 and 20 Torr.

To determine the effect of adding a coating to the membrane on filtration efficiency, CTC capture was evaluated using microsieve filters A, C, and X (5 µm round pores) with and without a zwitterionic anti-stick coating. Three-hundred bladder cancer cells were spiked into donated human blood and passed through the filter at the pressures shown in Table 4.

TABLE 4

Results of microsieve capture efficiency tests

| Filter Type | Pressure (Torr) | Flow Rate (ml/hr) | Run Time (min) | Yield |
|---|---|---|---|---|
| Uncoated C | 3-12 | 18-30 | 7 | 231 (77%) |
| Uncoated A | 20-36 | 24-28 | 9 | 140 (46.7%) |
| Uncoated X | 6-19 | 10-30 | 6 | 262 (87.3%) |
| Coated C | 5-18 | 30 | 5 | 157 (52.3%) |
| Coated A | 20 | 25-45 | 6 | 184 (61.3%) |
| Coated X | 10-25 | 15-27 | 7 | 237 (79.0%) |

Capture efficiency ranged from approximately 45% to nearly 80%, depending on pore size. The addition of the coating did not impair capture.

Example 3

Elution of CTCs

Figure 10:
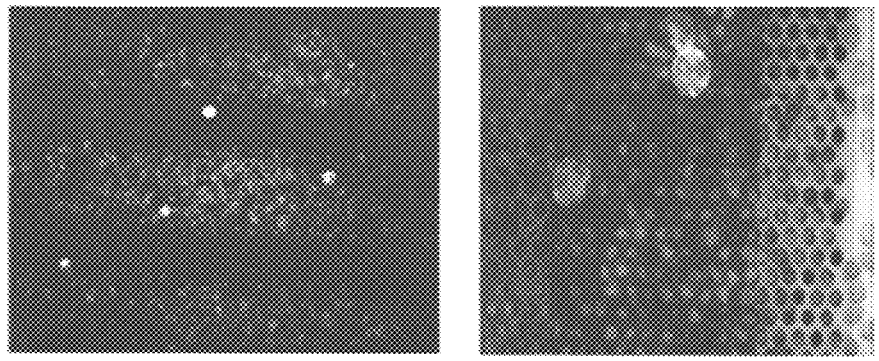
FIG. 10 are pictures of a live/dead cell viability assay of CTCs captured using a coated microsieve and subsequently eluted.
Figure 11:
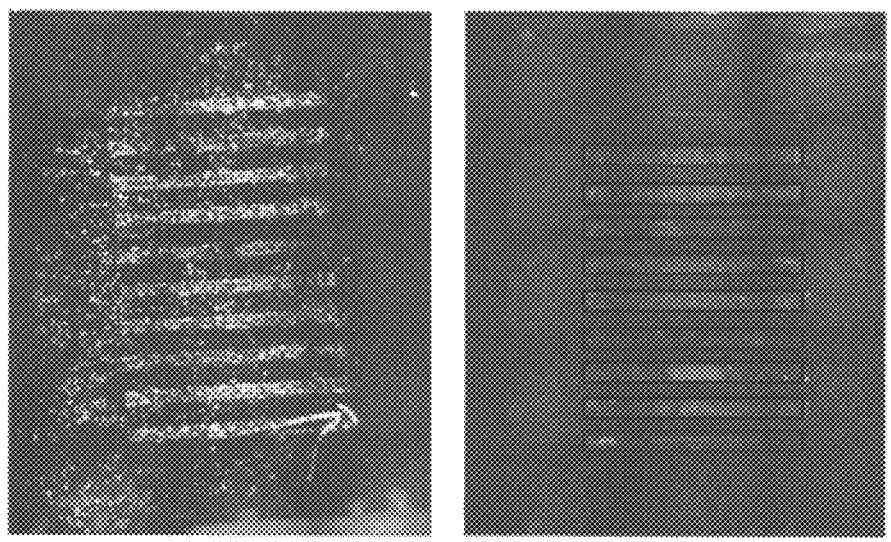
FIG. 11 are pictures showing CTCs on a microsieve prior to elution (left panel) and after elution (right panel).

Silicon nitride filters can oxidize over time, which can lead to cell adhesion, thereby and preventing elution of captured CTCs from the microsieve surface. This adhesion can be reduced using biocompatible zwitterionic coatings such as those used in stents and catheters. One-hundred prostate cancer cells were spiked into donor human blood and passed through a coated microsieve. As shown in FIG. 11 (left panel), numerous CTCs were captured on the filter. The captured CTCs were then eluted using a surfactant. FIG. 11 (right panel) shows that very few CTCs remained on the microsieve after elution. To determine whether eluted CTCs were viable, three-hundred prostate cancer cells were spiked into donated human blood and captured on a coated type C microsieve (pore size 3.5 µm by 8 µm). Cells were eluted and stained for viability. As shown in FIG. 10, live cells (green) significantly outnumbered dead cells (red).

Example 4

Blood Filtration Run

A subject's blood is drawn from and returned to the venous system through a standard dual-lumen catheter or access port or a double needle system. A peristaltic pump maintains a desired flow condition. The pump can be controlled to provide either constant flow or to maintain a desired pressure. The pump is located before the cross flow filter module (pushing blood through). The module comprises a retentate channel with a tapering height from 150 µm to 75 µm, a microsieve filter with 5 µm pores and an effective area of 2 cm². The blood flow has been continuously monitored for bubbles greater than a particular diameter by redundant bubble detectors. Flow is immediately shut off by a safety pinch valve if bubbles are detected. Pressure sensors have been used to monitor (e.g., continuously) the flow.

A control system has been used to determine if a sufficient numbers of CTCs have been concentrated and if a drain or collection cycle needs to be initiated. The collection cycle drains the retentate (CTC concentrate) and has been used for later analysis. The cycle may also be used to clear blood or other cellular components from the collection pathway prior to initiation of the collection, and at the end of the treatment cycle. A blood flow towards the module is set at 10 ml/min. A permeate flow of 9.2 ml/min is obtained (free of CTCs and with a reduced fraction of WBCs) and a retentate flow of about 0.8 ml/min blood (with CTCs and a major fraction of the WBCs) is led to a treatment chamber.

The treatment element here is an anti-EPCAM coated microsieve with a pore size of 10 µm. The capture efficiency of antibody-coated microsieves with a pore size of 10 µm was examined to capture CTCs. Anti-EpCAM (VU1D9) antibodies were attached to a polycarboxylate-coated microsieve. The polycarboxylate chains had a linear chain length of about 1200 nm. Part of the polycarboxylate chains was provided with polyethyeleneglycol side groups to reduce unspecific binding. After passage of about 48 ml of retentate blood through the treatment element the experiment was stopped, the microsieve was taken out of the treatment element, it was washed and stained. Microscopic counting using brightfield and fluorescence labeled anti-CK, anti-CD45 and DAPI (nuclear stain) images revealed the presence of one-hundred twenty-six CTCs attached to the microsieve surface.

Example 5

Dilution of Blood

It has been found advantageous to predilute the blood from the patient before applying cross-flow filtration: both the fraction of CTCs and WBCs have been found consequently higher when using a predilution fluid in specific cross-flow and dilution settings. In experiments using a microsieve with a pore size of 5 µm and 7 µm, respectively, the fraction of CTCs and WBCs is found to be 10% and 30% higher, in comparison with cross-flow filtration using undiluted blood.

The foregoing descriptions apply, in some cases, to examples generated in a laboratory, but these examples can be extended to production techniques. For example, where quantities and techniques apply to the laboratory examples, they should not be understood as limiting. In addition, although specific chemicals and materials have been disclosed herein, other chemicals and materials may also be employed according to one or more contemplated embodiments.

In this application, the use of the singular includes the plural unless specifically stated otherwise. In this application, the use of "or" means "and/or" unless stated otherwise. Furthermore, the use of the term "including", as well as other forms, such as "includes" and "included," is not limiting. Any range described herein will be understood to include the endpoints and all values between the endpoints.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, system, methods, and devices for extracorporeal blood processing for collecting circulating tumor cells. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicant intends to embrace all such alternatives, modifications, equivalents, and variations that are within the spirit and scope of the present invention.

The invention claimed is:

1. A method of treating a patient, comprising:
connecting a patient's blood stream to a circulating tumor cell (CTC) device, the device comprising:
a cross-flow module having:
a retentate channel with inlet and outlet ends;
a permeate channel adjacent to the retentate channel and having inlet and outlet ends; and
a CTC retention filter separating the permeate and retentate channels; and
a recirculation channel connecting the retentate channel outlet end with the retentate channel inlet end, the recirculation channel further comprising a treatment element, the CTC retention filter being constructed to retain at least white blood cells and CTCs;
filtering blood using the CTC retention filter so as to retain at least CTCs;
concentrating the CTCs in the fluid in the retentate channel; and
returning blood in the permeate channel to the patient.

2. The method of claim 1, wherein a flux of permeate passing through the filter is between 0.2 and 20 ml/cm²/sec.

3. The method of claim 1, wherein white blood cells and CTCs are separated in the retentate channel using said treatment element, the treatment element comprising filters having pore sizes of between 3 μm and 30 μm.

4. The method of claim 1, wherein the treatment element is a flow-along device in which the CTCs are immobilized on a surface of the treatment element, and the retentate fluid flows parallel to the surface on which the CTCs are immobilized.

5. The method of claim 4, wherein a cross-sectional diameter of the treatment element is less than about 500 μm.

6. The method of claim 1, wherein the treatment element is a flow-through device in which the CTCs are immobilized on a second filter, and white blood cells pass through the second filter.

7. The method of claim 6, wherein the treatment element comprises a microsieve with a pore size larger than 10 μm.

8. The method of claim 7, wherein the treatment element comprises antibodies that bind the CTCs in the retentate fluid.

9. The method of claim 8, wherein the antibodies comprise one or more of an anti-EPCAM antibody, anti-EFGR antibody, or other antibody capable of binding CTCs.

10. The method of claim 9, wherein the antibodies are immobilized on the surface of the second filter.

11. The method of claim 10, wherein the antibodies are immobilized on a hydrogel layer on the surface of the second filter.

12. The method of claim 1, wherein the device is capable of filtering at least 1 L of bodily fluid.

13. The method of claim 1, wherein the permeate channel is in fluid contact with the patient and the filtered blood is returned to the patient via the permeate channel.

14. The method of claim 1, wherein the blood is pre-diluted with a dilution fluid before entering the cross-flow module.

15. The method of claim 14, wherein added dilution fluid exiting the cross-flow module is removed using a membrane filter having a low molecular weight cut-off of less than 1,000 Daltons, and the membrane filter is provided with chemical affinity modifications to retain cytokines or other materials so as to achieve a specific composition of the blood or other bodily fluid for return to the patient.

16. The method of claim 1, further comprising, exposing white blood cells to concentrated CTCs in the treatment element, wherein the white blood cells exposed to CTCs include at least one of T-lymphocytes and natural killer cells (NK cells).

17. The method of claim 16, further comprising exposing white blood cells in the treatment element to additional cytokines that stimulate and mature the white blood cells, wherein the additional cytokines comprise at least one of IL8, IL12, IL15 and interferon.

18. The method of claim 1, wherein the treatment element comprises a second filter for separating CTCs from the retentate fluid, the CTC retention filter and/or the second filter being provided with an anti-EPCAM antibody, an anti-EFGR antibody, or other antibody that binds CTCs, wherein the antibodies are immobilized on a surface of the corresponding filter.

19. The method of claim 18, wherein the antibodies are immobilized on a brush-like hydrogel layer on the surface of the corresponding filter.

* * * * *